(12) United States Patent
Dirks et al.

(10) Patent No.: US 11,001,839 B2
(45) Date of Patent: May 11, 2021

(54) METHOD FOR MAKING CHROMOSOME SUBSTITUTION LIBRARIES

(71) Applicant: RIJK ZWAAN ZAADTEELT EN ZAADHANDEL B.V., De Lier (NL)

(72) Inventors: Robert Hélène Ghislain Dirks, De Lier (NL); Evert Willem Gutteling, De Lier (NL); Geo Velikkakam James, De Lier (NL); Remco Abran Ursem, De Lier (NL)

(73) Assignee: RIJK ZWAAN ZAADTEELT ENZAADHANDEL B.V., De Lier (NL)

( * ) Notice: Subject to any disclaimer, the term of this patent is extended or adjusted under 35 U.S.C. 154(b) by 183 days.

(21) Appl. No.: 15/373,741

(22) Filed: Dec. 9, 2016

(65) Prior Publication Data

US 2017/0145408 A1    May 25, 2017

Related U.S. Application Data

(63) Continuation-in-part of application No. PCT/EP2015/065636, filed on Jul. 8, 2015.

(30) Foreign Application Priority Data

Jul. 8, 2014   (EP) .................................... 14176208
Nov. 10, 2014   (EP) .................................... 14192516

(51) Int. Cl.
*A01H 1/08* (2006.01)
*A01H 1/04* (2006.01)
*C12N 15/10* (2006.01)
*A01H 1/02* (2006.01)
*C12N 15/82* (2006.01)

(52) U.S. Cl.
CPC ........... *C12N 15/1093* (2013.01); *A01H 1/02* (2013.01); *A01H 1/04* (2013.01); *A01H 1/08* (2013.01); *C12N 15/8287* (2013.01)

(58) Field of Classification Search
None
See application file for complete search history.

(56) References Cited

FOREIGN PATENT DOCUMENTS

WO    WO-2014076249 A1 *    5/2014    ............... A01H 5/00

OTHER PUBLICATIONS

Wijnker et al 2012 Nature Genetics 44:467-470 provided by Applicant (Year: 2012).*
International Search Report and Written Opinion of the International Searching Authority dated Sep. 11, 2015, which issued during prosecution of International Application No. PCT/EP2015/065636.
Dirks, et al. "Reverse breeding: a novel breeding approach based on engineered meiosis" Plant Biotechnology Journal, 2009, 7(9):837-845.
Perera, et al. "Chromosome substitution lines for the analysis of heterosis in *Arabidopsis thaliana*" J. Natn. Sci. Foundation Sri Lanka, 2008, 36(4):275-280.
Wijnker, et al. "Hybrid recreation by reverse breeding in *Arabidopsis thaliana*" Nature Protocols, 2014, 9(4):761-772.
Wijnker, et al. "Reverse breeding in *Arabidopsis thaliana* generates homozygous parental lines from a heterozygous plant" Nature Genetics, 2012, 44(4):468-471.

* cited by examiner

*Primary Examiner* — Brent T Page
(74) *Attorney, Agent, or Firm* — Duane Morris LLP; Thomas J. Kowalski; Deborah L. Lu (57) ABSTRACT

The invention relates to a method for producing a chromosome substitution library, comprising: a) producing a population of DH lines from an at least partially heterozygous starting organism; b) identifying a first DH line in the population that has at least one non-recombined chromosome pair; c) identifying a matching second DH line in the population that has at least one non-recombined chromosome pair that is the same as the non-recombined chromosome pair of the first DH line, and at least one non-recombined chromosome pair that is different from the non-recombined chromosome pair of the first DH line; d) selecting the first DH line and the second DH line as a pair of parents, the progeny of which has at least three non-recombined chromosomes, at least two of which form a pair; e) repeating steps b), c) and d) one or more times on the DH population of the heterozygous starting organism, or repeating steps a)-d) on a DH population produced from a progeny plant of a pair of parents selected in step d), until preferably all chromosomes from the selected DH lines are non-recombined and preferably all possible combinations of the parental chromosomes are selected, to assemble a library of chromosome substitution lines. The invention further relates to the libraries thus obtained.

10 Claims, 5 Drawing Sheets
(1 of 5 Drawing Sheet(s) Filed in Color)

METHOD FOR MAKING CHROMOSOME SUBSTITUTION LIBRARIES

RELATED APPLICATIONS AND INCORPORATION BY REFERENCE

This application is a continuation-in-part application of International Patent Application Serial No. PCT/EP2015/065636 filed Jul. 8, 2015, which published as PCT Publication No. WO 2016/005467 on Jan. 14, 2016, which claims benefit of European patent application Serial Nos. 14176208.8 filed Jul. 8, 2014 and 14192516.4 filed Nov. 10, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a method for making chromosome substitution libraries.

BACKGROUND OF THE INVENTION

In plants and animals alike, chromosomal recombination during meiosis ensures that new combinations of traits emerge in every consecutive generation. In the wild, this randomized shuffling of genomes is the driving force behind evolutionary adaptation to changing environments, and it is an essential mechanism for the successful survival and competitiveness of species. The sexual offspring of two genetically distinct and dissimilar parents inherit a unique new combination of traits, and natural selection will ultimately determine which of the infinite number of possible combinations of traits will have the best fitness in that specific environment. It is trial and error on a massive scale, and in favourable climatic conditions it may take dozens of generations before certain traits get the upper hand in a population. Superior combinations of traits will be preferentially passed on to the next generations, and they will enhance the biological success of the species in its biotope.

In cultivated species, however, the main driving force behind breeding is human preference and selection. Plant breeders attempt to combine as many elite traits in a single genome as possible, while at the same time eliminating as many undesirable traits as possible. On an industrial scale this genetic stacking (pyramiding) should happen as efficiently as possible. Ideally, it should only take minimal efforts and a limited number of generations to obtain the desired combination of traits. Because plant growers usually ensure that cultivated plants are not subjected to natural competition with other plants ("weeds") in the field or greenhouse (by weeding and/or applying herbicides), and that they do not need to spread their pollen and seeds as efficiently as possible, human selection often leads to very different preferences than the ones that would be successful in the wild.

Some traits are important in both cultivated and wild conditions, such as disease resistance, enhanced growth speed, drought, cold and heat tolerance, and the ability to produce many healthy seeds under a wide range of climatic conditions. However, in contrast to Mother Nature, plant breeders often also select for traits that are not directly beneficial for the plant species itself, but only for the seed company, for the growers, and for the consumers that will ultimately buy the harvested products from these plants. There are many traits with a purely commercial value, including e.g. novel colours of fruits and leaves, higher levels of specific chemical compounds, non-shedding of grains from cereal stalks, male sterility, etc.

Plant breeding has already come a long way since the time of our ancestors, when they collected seeds from interesting-looking individual plants in the wild, with the intention to sow them on a plot of stripped land at the start of the next growing season. Marker-assisted breeding, genome sequencing, (site-directed) mutagenesis methods and advancing knowledge about the genetic basis of important traits are emerging as a powerful toolbox, which helps plant breeders in their quest to further speed up the pyramiding of elite traits into a single genome. Nevertheless, one major obstacle remains: plant genomes are reshuffled during every single meiosis, thereby causing the random segregation of the traits (in the F2 generation) that had been brought together in the previous generation. While the meiotic segregation of traits is a fundamental asset for plant survival in the wild, it creates a numbers game dilemma, and may be a nuisance for plant breeders.

Several solutions have been proposed to solve this conflict between the plant species' interests and the breeder's interests.

The most straightforward (but commercially not so attractive) manner is to repeatedly cross the F1 plants derived from the cross of two selected parent plants back to one of the parent plants, and in every generation again select for individuals that harbor all of the desired traits, or as many as practically possible. Selection may be done on the basis of phenotypical characteristics, and/or with the help of molecular markers associated with the various traits. This classical breeding process is very time-consuming, as it usually takes at least four to six backcross generations and a large progeny to obtain a line that is largely homozygous and resembling the parent plant, and into which one or more desired traits from the donor plant have been introgressed and fixed. While some annual crops, such as lettuce, have a relatively short life cycle, other (biannual) crops, such as carrot, require two years to produce seed. The generation of a new commercial variety can thus easily take from about 8 to about 20 years, depending on the species.

Another approach is the introduction of one or more isolated genes into plant genomes. By introducing a transgene directly into an elite line's genome, one does not need to cross that elite line with another line that naturally carries the trait of interest, and thereby the segregation of the combined elite traits (which are typically already present in a homozygous state) is avoided.

These transgenes are typically inherited in a dominant fashion. They may correspond to genes, gene clusters or intergenic sequences that occur naturally in the same plant species or in a plant species that can be crossed therewith to give rise to fertile offspring. This is known as cisgenesis. Alternatively, they may correspond to synthetic genes or to DNA-fragments from organisms that cannot naturally cross with the plant species of interest, such as plants from another family, or organisms from different taxa, such as animals, fungi, viruses or bacteria. This is known as transgenesis. These DNA-sequences are either introduced unchanged into the genome of the plant species of interest, or they are altered in some way, for example by recombinant DNA technology with or without mutagenesis.

Transgenic, recombinant DNA technologies allow researchers to combine multiple DNA-constructs into the genome of the same plant, and thus to pyramid different traits. These constructs can be easily traced back in the breeding pipelines, and their presence can typically be selected for on a large-scale, by means of selection markers (e.g. herbicide or antibiotics resistance). This approach can ultimately result in the creation of plants that harbor a multitude of selected traits, by combinatorial stacking/pyramiding of transgenes encoding these desired traits.

However, such transgenic approaches have a number of disadvantages. Often it cannot be predicted in advance whether a transgene may negatively influence plant performance in unsuspected ways. Also, the effect and/or functionality of a given transgene often strongly depends on the exact position in the plant genome in which it has been inserted. For any genetically modified lead to receive approval for commercial use and animal and/or human consumption, it needs to undergo very extensive regulatory procedures, which are tremendously expensive and time-consuming. Authorization will often only be granted for a specific transgenic insertion event in a given genome. The accumulation of multiple transgenes makes this process even more costly, tedious and complex. Moreover, in important parts of the worldwide food market, transgenic food is not allowed for human consumption, and not appreciated by the public.

Another approach for combining desired traits is to partially or completely suppress the mechanism of cross-over (recombination) during meiosis. By ensuring that the mechanisms of double strand breaks and/or chromosome pairing and/or strand exchange during meiosis do not occur at the normal, wildtype level, or that they are completely absent, the parental chromosomes are passed on to the spores in a non-recombined, intact manner. Especially when one combines this approach with the production of Doubled Haploid (DH) lines from the spores that have been produced in the absence of recombination, it becomes possible to efficiently make novel combinations of the parental genomes. This approach is known as Reverse Breeding (WO03/017753; Dirks et al. 2009, *Plant Biotech J* 7: 837-845). A drawback of this method, however, is that the lack of chromosome pairing results in a random distribution of the chromatids across the four daughter cells that typically result from meiosis. The more chromosomes a species harbours, the smaller the probability for a spore to be euploid (containing a complete chromosome set). When a spore or gamete is euploid, it contains the full complement of haploid chromosomes (n) typical for the species' genome. In principle only euploid spores can successfully carry out fertilization or regenerate into viable plants, and aneuploidy (the presence of more than the full complement of haploid chromosomes specific to the species, or of less than the full complement of haploid chromosomes specific to the species) is therefore highly undesired at this stage. Aneuploidy is usually eliminated spontaneously by nature, and the occurrence of aneuploidy causes a population of spores to contain a low frequency of normal, viable spores, which negatively affects the efficiency of inducing embryogenesis from the low number of surviving spores. Another potential disadvantage of this method is that it relies on the action of a transgenic construct, which may give the resulting products a "genetically modified organism" status in certain regions of the world, under the current regulations, even when the transgene itself is no longer present in said products.

Another approach to avoid the segregation of traits during the breeding process is the creation of chromosome substitution lines from a pair of parental lines. As described previously (WO2014/001467), a chromosome substitution line is ideally a Doubled Haploid (DH) line, whose fully homozygous genome consists of intact and complete chromosomes that were inherited from the parents of the heterozygous starting plant from whose spores the DH had been created, without the occurrence of recombination.

Citation or identification of any document in this application is not an admission that such document is available as prior art to the present invention.

SUMMARY OF THE INVENTION

Doubled Haploids (DHs) can be created from the spores of a heterozygous starting plant by means of e.g. androgenesis or gynogenesis protocols, or through the use of haploid inducer systems. The genome of these haploid plants is subsequently doubled. Genome doubling, which may occur spontaneously, or through the addition of mitosis-blocking chemicals such as colchicine, oryzalin or trifluralin, leads to the formation of doubled haploid plants (DH plants, DHs), which are able to produce seeds. In this manner the doubled haploid lines are immortalized.

The DHs resulting from this method have a fully homozygous genome that consists of intact chromosomes that were inherited from the parents of the heterozygous starting plant, without the occurrence of recombination. There are various possible combinations of the original parental chromosomes, and the number of different DH lines depends entirely on the chromosome number of the plant species.

Either the DHs correspond exactly to one of the two parents of the heterozygous starting plant, or their genome consists of one or more chromosomes of the first parent combined with the remaining chromosome set of the second parent, to reach the full haploid chromosome number of the species. Such DHs are chromosome substitution lines, in which, when compared to one of the original parents of the heterozygous starting plant, at least one chromosome has been substituted with the intact and complete corresponding chromosome from the other parent, without the occurrence of cross-over. A complete chromosome substitution library may comprise all chromosome substitution lines that can be obtained from a given heterozygous starting plant, and hence all possible combinations of chromosomes from both parental lines of that heterozygous plant.

A complete chromosome substitution library can e.g. be obtained directly from a given heterozygous starting plant by means of the partial or complete suppression of meiotic recombination (as in Reverse Breeding), or alternatively, especially when the chromosome number of the species is large, two or more successive rounds of partial or complete suppression of meiotic recombination (resembling two or more successive rounds of Reverse Breeding) may be required to obtain all possible chromosome substitution lines.

In the latter case, two different chromosome substitution lines, obtained through the partial or complete suppression of meiotic recombination, can be crossed, to give rise to a hybrid plant in which some of the chromosomes are present in a homozygous state, while other chromosomes are present in a heterozygous state. Application of the partial or complete suppression of meiotic recombination in this new hybrid plant results in the creation of additional chromosome substitution lines. This way of using meiotic recombination suppression in multiple steps reduces the number of heterozygous chromosomes and therefore increases very significantly the probability for obtaining desired unique karyotypes (specific combinations of the parental chromosomes), and for obtaining a complete chromosome substitution library.

This concept is best illustrated with a theoretical example, using a heterozygous starting plant belonging to a species with 10 chromosome pairs (such as e.g. maize). When doubled haploids are generated from this starting F1 hybrid with partial or complete suppression of meiotic recombination, the transfer of the chromosomes to the DHs typically occurs according to a binomial distribution. The overall probability of obtaining a DH line that contains 5 non-recombinant parental chromosomes from the first original parent of the heterozygous starting plant and 5 non-recombinant parental chromosomes from the second original parent of the heterozygous starting plant is 252 times higher than the probability of obtaining a DH that contains 10 non-recombinant chromosomes from just one of the original parents. This is caused by the fact that—for a species with 10 chromosome pairs—there are only two possibilities for obtaining 10 non-recombinant chromosomes (one option from either parent), but 252 different possibilities (permutations) to obtain a DH line that contains 5 non-recombinant parental chromosomes from the first original parent and 5 non-recombinant parental chromosomes from the second original parent (e.g. chromosomes I, II, III, IV and V from the first parent, combined with chromosomes VI, VII, VIII, IX and X from the second parent is one possibility to obtain a euploid haploid genome which may comprise 5 chromosomes from each original parent of the F1 hybrid; a second possibility is the combination of chromosomes I, III, IV, V and VI from the first parent with chromosomes II, VII, VIII, IX and X from the second parent; and in this manner 252 different combinations are possible for a euploid doubled haploid genome which may comprise 5 chromosomes from each original parent of the F1 hybrid).

If a complete chromosome substitution library has not been obtained after a first round of Reverse Breeding, specific pairwise combinations of chromosome substitution lines that had been obtained may be used as starting material to obtain the remaining chromosome substitution lines, in a second or subsequent round of Reverse Breeding. When specific, selected pairs of doubled haploid chromosome substitution lines are crossed, this will result in progeny plants that are homozygous for some of the chromosomes, and heterozygous for the other chromosomes. For example, a first DH plant harbouring chromosomes I, II, III, IV, V and VI from the first parent and chromosomes VII, VIII, IX and X from the second parent, can be crossed to a second DH plant harbouring chromosomes I, II, III, IV, V, IX and X from the first parent, and chromosomes VI, VII and VIII from the second parent. The progeny resulting from this cross will be homozygous for chromosomes I, II, III, IV, V, VII and VIII, and heterozygous for chromosomes VI, IX and X. This approach thus reduces the complexity of the genome, because instead of 10 heterozygous chromosomes the resulting progeny (in this example) only have 3 heterozygous chromosomes, and 7 homozygous chromosomes. When Reverse Breeding is performed on such a progeny plant, it will behave as if it were a plant with only 3 chromosome pairs, as the other 7 chromosome pairs have been fixed in a homozygous state. This principle is further explained in Example 4.

When several of these targeted DH combinations are made, this approach will greatly increase the probability of identifying all possible combinations of the parental chromosomes among the DH population resulting from this second round of Reverse Breeding. The use of two or more successive rounds of Reverse Breeding thus conveniently allows the construction of complete chromosome substitution libraries for species with large chromosome numbers, without a need for screening excessively large DH populations.

In the research leading to the present invention, it was surprisingly found that the above described methodology for creating chromosome substitution libraries may also be carried out without transgenes, i.e. without the active partial or complete suppression of meiotic recombination. The invention is based on the surprising finding that in a subset of the spores in a population of spores produced by a given non-homozygous plant, one or more chromosomes remain non-recombined, even without external interference with the meiotic recombination mechanism. The inventors contemplated that such non-recombined chromosomes can be identified by means of molecular techniques (such as molecular markers or DNA-sequencing technologies). Major advantages of the present invention are the absence of aneuploidy (causing severely reduced male and/or female fertility), the time gained by not having to create transgenic plants in which meiotic cross-over is suppressed (and to identify plants that are hemizygous for a single copy of a transgene), and the non-GMO (non-transgenic) status of the products obtainable with the method.

The absence of aneuploidy means that the spores produced by said plants are balanced, i.e. that they contain the full complement of haploid chromosomes specific to the species. This solves the most important problem in Reverse Breeding, namely the occurrence of aneuploid, unbalanced spores, which can generally not give rise to viable plants through in vitro embryogenesis and which can also not pollinate ovules efficiently to give rise to viable embryos. The elimination of aneuploidy is a direct result of the fact that meiotic recombination is not suppressed, such that all steps of meiosis can proceed without interference, and male meiosis thus results in the formation of tetrads of balanced spores. This advantage ensures that the current invention can be applied to any plant species, regardless of the number of chromosomes.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

DETAILED DESCRIPTION OF THE INVENTION

The present invention thus relates to a method for producing a chromosome substitution library, which may comprise:
  a) producing a population of DH lines from an at least partially heterozygous starting organism;
  b) identifying a first DH line in the population that has at least one non-recombined chromosome pair;
  c) identifying a matching second DH line in the population that has at least one non-recombined chromosome pair that is the same as the non-recombined chromosome pair of the first DH line, and at least one non-recombined chromosome pair that is different from the non-recombined chromosome pair of the first DH line;
  d) selecting the first DH line and the second DH line as a pair of parents, the progeny of which has at least three non-recombined chromosomes, at least two of which form a pair;
  e) repeating steps b), c) and d) one or more times on the DH population of the heterozygous starting organism, or repeating steps a)-d) on a DH population produced from a progeny plant of a pair of parents selected in step d), until preferably all chromosomes from the selected DH lines are non-recombined and preferably all possible combinations of the parental chromosomes are selected, to assemble a library of chromosome substitution lines.

The present invention is especially applicable to plants. The invention thus also relates to a method for producing a chromosome substitution library which may comprise:
  a) producing a population of DH lines from an at least partially heterozygous starting plant;
  b) identifying a first DH line in the population that has at least one non-recombined chromosome pair;
  c) identifying a matching second DH line in the population that has at least one non-recombined chromosome pair that is the same as the non-recombined chromosome pair of the first DH line, and at least one non-recombined chromosome pair that is different from the non-recombined chromosome pair of the first DH line;
  d) selecting the first DH line and the second DH line as a pair of parents, the progeny of which has at least three non-recombined chromosomes, at least two of which form a pair;
  e) repeating steps b), c) and d) one or more times on the DH population of the heterozygous starting plant, or repeating steps a)-d) on a DH population produced from a progeny plant of a pair of parents selected in step d), until preferably all chromosomes from the selected DH lines are non-recombined and preferably all possible combinations of the parental chromosomes are selected, to assemble a library of chromosome substitution lines.

In a preferred embodiment, at least one DH line is produced from an F1 hybrid that, by chance, contains only complete and unaltered chromosomes from the original parents. The preferred chromosomal composition is a combination of chromosomes from both parents so that the parental lines are not recreated, when said parents of the hybrid are already available. The binomial distribution allows prediction of the genotypes (chromosomal composition) in function of their probability of occurrence. In this embodiment, none of the chromosomes have undergone recombination, but the application/usefulness is not restricted to lines with a full set of non-recombinant chromosomes. Also DH lines that contain all but one, all but 2, all but 3, etcetera non-recombinant chromosomes that were derived from the original parents can be used to combine with the original parental lines or with each other, or with DH lines that have a full set of non-recombinant chromosomes. The best combination of the second cycle of DH line production and the identification of suitable new DH lines to complete the Chromosome Substitution Library can be calculated by means of specialised software (a process which one may call "combinatorial optimisation").

Surprisingly, as illustrated in example 4 for a genome containing 10 chromosome pairs, the probability for identifying a DH line with one chromosome out of 10 recombined between the original parental chromosomes, is 10 times higher than the probability to identify one DH line without any recombinant chromosomes. The same order of magnitude can be found for respectively 5 and 7 chromosome pairs (approximately a 5 times and 7 times higher probability). The occurrence of one recombinant chromosome in a DH line with otherwise non-recombinant chromosomes does not jeopardize the concept of creating chromosome substitution libraries with full sets of complete non-recombinant chromosomes.

In another preferred embodiment, at least one of the DH lines selected in step d) is genetically identical to one of the two parents of the at least partially heterozygous starting organism (also referred to as "the starting hybrid"), or instead of said DH line that is genetically identical to the parent the original parent is used as one member of the pair of parents in step d). In this embodiment the procedure of creating an optionally complete chromosome substitution library is accelerated, because the genome of a parent of the starting hybrid by definition possesses one complete set of non-recombined parental chromosomes. When one of the parents of the starting hybrid is crossed to a DH line with at least one non-recombined chromosome derived from that same parent, the resulting F1 offspring will be homozygous for said at least one parental chromosome, and heterozygous for all other parental (non-recombined) chromosomes from that parent.

A parent of the starting hybrid may be selected from among the DH lines obtained in step a) of the claimed method (as e.g. illustrated in Example 2), but it may also be a sexual offspring of the original parent of the starting hybrid, obtained through selfing. The latter approach is possible when at least one of the two parents of the starting hybrid is known and available to the experimenter, and when said parent is substantially homozygous.

In the claimed method, DHs can be produced from the spores of the heterozygous starting organism by first creating haploid plants of the spores by means of androgenesis, such as microspore culture or anther culture, by gynogenesis, or by inducing the loss of maternal or paternal chromosomes from a zygote resulting from a fertilization event, and then doubling the genome of the haploid plants thus obtained. The skilled person is very familiar with these non-transgenic methods of DH production, and he knows which method works best in his favourite plant species.

Genome doubling may occur spontaneously, or it may be induced by the application of chemicals, such as colchicine, oryzalin or trifluralin. These chemicals disrupt spindle formation during mitosis, and are typically used for the blocking of mitosis.

The loss of maternal chromosomes from a zygote resulting from a fertilization event can be induced by using a haploid inducer line as the female in a cross. Haploid inducer systems have been described in various plant species. In one embodiment, the female is a plant of a different species. In interspecific crosses loss of the genome of one of the parents has often been observed, such as in the cross between wheat and pearl millet, between barley and *Hordeum bulbosum*, and between tobacco (*Nicotiana tabacum*) and *Nicotiana africana*.

The female plant can also be a transgenic plant that may comprise a heterologous transgene expression cassette, the expression cassette which may comprise a promoter operably linked to a polynucleotide encoding a recombinantly altered CENH3, CENPC, MIS12, NDC80 or NUF2 polypeptide, and having a corresponding inactivated endogenous CENH3, CENPC, MIS12, NDC80 or NUF2 gene. This approach for obtaining haploid plants through genome elimination has been first described in *Arabidopsis thaliana* (Maruthachalam Ravi & Simon W. L. Chan; *Haploid plants produced by centromere-mediated genome elimination;* Nature 464 (2010), 615-619; US-2011/0083202; WO2011/044132), and it is broadly applicable in plants.

Selecting matching DH lines with at least one non-recombined chromosome may be done in any manner known to the skilled person. For example, they can be selected on the basis of phenotypical characteristics, and/or on the basis of genomic testing, such as by DNA-marker analysis, Single Nucleotide Polymorphism (SNP) detection, DNA-sequencing, etc.

As an alternative to selecting DHs with non-recombined parental chromosomes from among a population in which meiotic recombination has progressed without external interference, it is also possible to actively limit the average number of cross-over events per chromosome to approximately one cross-over per bivalent. This may be done by treatment of the spores, around the time of meiosis, with for example puromycin, and this approach greatly reduces the complexity of the possible outcomes of the meiotic process, and hence reduces the genetic complexity among a DH population. Puromycin is a protein synthesis inhibitor that causes meiotic arrest in spores. Its inhibitory action can be reversed.

The recombination frequency and therefore map size and distance between loci is dependent on the temperature at which plants are grown. This means that the genetic map size in species with chromosomes with genetic map lengths of more than 100 cM (which corresponds to more than one crossover in the tetravalent stage) at optimal growing temperature, can be modified by putting them in lower temperature regimes. This means that the map size of chromosomes larger than 100 cM can be significantly reduced. In a preferred embodiment this reduction is to about 100 cM (=one crossover event in the tetravalent stage). (See also Francis K, Lam S, Harrison B, Bey A, Berchwitz, L and Copenhaver G (2007) Pollen tetrad-based visual assay for meiotic recombination in *Arabidopsis*. PNAS Vol 104, no 10, 3913-3918).

The present invention relates to a method for producing a chromosome substitution library from a DH population derived from a starting hybrid, which may comprise:

a) crossing DH lines to each other and/or to the parents of the starting hybrid, to obtain a second generation donor population for a second cycle of DH production;
b) producing a population of DHs from the spores of the F1 progeny of selected DHs;
c) crossing DH lines to each other and/or to the parents of the starting hybrid, to obtain a third generation donor population for a third cycle of DH production;
d) repeating steps b) and c) one or more times until a suitably complete chromosome substitution library has been created.

The invention further relates to a method for producing chromosome substitution lines from a DH population.

In the claimed method, the term "a chromosome that is the same" refers to a chromosome that has been derived from the same parent of the hybrid organism and that has the same chromosome number in that species (=chromosome I, II, . . . ). In the claimed method, the term "a chromosome that is different/dissimilar" refers to a chromosome that has been derived from the same parent of the hybrid organism and that has a different chromosome number in that species.

In the claimed method, the progeny of the first and second DH lines has at least three non-recombined chromosomes, at least two of which form a pair. This means that said progeny has inherited both copies of at least one chromosome from one of the parents of the starting hybrid, which copies form a pair of chromosomes, and at least one copy of another chromosome from that same parent of the starting hybrid. Suitably said progeny has inherited both copies of one chromosome, of two chromosomes, of three chromosomes, etcetera, up to (n−1) chromosomes, with n being the number of haploid chromosomes in that species. Effectively, this reduces the complexity of the progeny's genome, because one or more of its chromosomes is present in a completely homozygous state. When DH lines are produced from the spores of such a plant, meiotic recombination will not lead to detectable changes in the genetic composition of said one or more chromosomes. When the DH lines are chosen efficiently (e.g. through combinatorial optimisation), this approach makes it possible to quickly obtain a full chromosome substitution library for any given starting hybrid. The larger the population of DH lines, the easier and faster this procedure can be completed.

The present invention further relates to a method for producing a chromosome substitution library, which may comprise:
a) producing a population of DH lines from an at least partially heterozygous starting organism;
b) identifying a first DH line in the population that has at least one non-recombined chromosome pair;
c) identifying a matching second DH line in the population that has at least one non-recombined chromosome pair that is the same as the non-recombined chromosome pair of the first DH line, and at least one non-recombined chromosome pair that is different from the non-recombined chromosome pair of the first DH line;
d) selecting the first DH line and the second DH line as a pair of parents, the progeny of which has at least three non-recombined chromosomes, at least two of which form a pair;
e) repeating steps b), c) and d) one or more times on the DH population of the heterozygous starting organism, or repeating steps a)-d) on a DH population produced from a progeny plant of a pair of parents selected in step d), until preferably all chromosomes from the selected DH lines are non-recombined and preferably all possible combinations of the parental chromosomes are selected, to assemble a library of chromosome substitution lines, wherein the at least partially heterozygous starting organism is a plant.

In a preferred embodiment, the wording "at least two of the non-recombined chromosomes" that form a pair in step d) corresponds to all chromosomes of the plant (=n). In decreasing preference, this wording also corresponds to (n−1), (n−2) or (n−3), etc. In the situation wherein "at least two" corresponds to n, the progeny of the identified DH lines may comprise n intact, non-recombined chromosomes, and no recombined chromosomes. In the situation wherein "at least two" corresponds to (n−1), the progeny of the identified DH lines may comprise (n−1) intact, non-recombined chromosomes, and one recombined chromosome. In the case of *Arabidopsis*, n equals 5, and (n−1) thus equals 4.

The present invention also relates to a library of substitution lines, obtainable by the method described above. Because the method for obtaining said library of substitution lines does not contain any transgenic steps, the library itself is also non-transgenic. This is an important difference with the transgenic library of substitution lines that has previously been produced from an *Arabidopsis* Col-0×Ler hybrid starting plant (Wijnker et al 2012, *Nature Genet.* 44: 467-471).

This invention further relates to a non-transgenic library of substitution lines, obtainable by the method described above, wherein in each of the substitution lines one chromosome pair is derived from the first parent of the heterozygous starting organism and the other chromosome pairs are derived from the second parent of the heterozygous starting organism.

The present invention further relates to a non-transgenic line that may comprise in its genome at least one non-recombinant chromosome from either parent, or from both parents. It also relates to a (partial or complete) library of lines that each may comprise in their genome at least one non-recombinant chromosome from either parent, or from both parents.

The present invention can be applied to all plant species for which DHs can be made.

Crop species on which this invention can be practised include but are not limited to tobacco, poplar, maize, wheat, barley, rice, sorghum, sugar beet, oilseed rape, ryegrass, sunflower, soybean, tomato, cucumber, gherkin, corn salad, rocket, spinach, pepper, *petunia*, potato, eggplant, melon, watermelon, carrot, radish, lettuce, vegetable *Brassica* species (cabbage, cauliflower, broccoli, kohlrabi, Brussels sprouts), leek, bean, pea, endive, chicory, onion, strawberry, fennel, table beet, celery, celeriac, asparagus, sunflower, grape vine, cassava, cherry, apple, pear, peach, banana, tulip, *petunia*, rose, and *Chrysanthemum*.

Chromosome substitution lines (also termed "substitution lines") are lines that harbour in their genome at least one chromosome from another line or plant. One or two copies of the original chromosome or chromosomes from a first line or plant has/have been replaced (substituted) by the corresponding copy or copies of that chromosome or chromosomes from another line or plant. The remaining chromosomes are identical to those that were originally present in the first line or plant.

In the context of the present invention, a library of substitution lines (also termed "a library of chromosome substitution lines" or "a chromosome substitution library") is intended to mean a population of chromosome substitution lines which may comprise individual chromosome substitution lines that each harbour a different combination of intact chromosomes from two different parental origins.

A complete chromosome substitution library may comprise all possible combinations of parental chromosomes from two different parental origins. For instance, in the diploid species Arabidopsis thaliana with 5 chromosome pairs a complete library of chromosome substitution lines may comprise $2^x=2^5=32$ members (lines). All genetic variation that is contained in the starting F1 plant is present in this small library of 32 plants. A complete substitution library allows the detection of epistatic interactions in an unprecedented way. A NIL library with representation of all chromosomal regions would require a near infinite number of crosses and backcrosses to even remotely approximate this situation.

It is important to notice that chromosome substitution libraries (and hence also a method to create them) will revolutionise plant breeding: in the classical breeding schemes, plants are selected from a segregating population such as F2, or in special cases RILs, BILs, NILs, MAGIC, HIFs and other populations for mapping purposes or for introgressing specific genes for specific desired traits. In all such cases, the number of possible genotypes of such populations is sheer infinite, and because this exceeds the breeder's or geneticist's capacity he is forced to operate in a reductionistic setup. He can thus only work with tiny subsets of the entire pool of possible genotypes, which are very often not representative or sufficient to obtain the best possible outcome of his breeding activities. Unlike in the classical approach, a chromosome substitution library contains all possible combinations of alleles as they were present in the different chromosomes of the original parental lines, and by consequence the geneticist can now operate non-reductionistically.

Many different applications can be envisioned for the present invention. One application is the quick and efficient mapping of traits to specific chromosomes. When phenotypically comparing the different lines within a chromosome substitution library, it becomes quite feasible to identify the chromosome(s) on which the gene(s) and/or Quantitative Trait Loci (QTLs) underlying the phenotypic trait of interest is (are) located, by comparing the chromosomes that are present in each of the lines that have the phenotype of interest, and in those that do not have the phenotype of interest. Another application, with a similar approach, is the study of epistatic interactions. Yet another application is single-chromosome breeding (breeding per chromosome), wherein a breeder can e.g. decide which parental version of each chromosome of the starting hybrid is included in a new hybrid. In this manner the starting hybrid can also be genetically improved, by e.g. replacing one parental copy of a chromosome by the corresponding copy of that chromosome from the other parent, if that second copy is superior over the first copy. This approach leads to the creation of hybrids that are e.g. heterozygous for all but one chromosome, with the remaining chromosome being homozygous and derived from only one of the two parents of the starting hybrid.

The present application can also be used to create sub-hybrid libraries. The invention can also be applied for mapping heterosis, for mapping combining ability, etc.

The present invention can also be applied in the context of Line Design (an invention described in WO2014/001467), to create so-called tribrids or multibrids (polybrids) that are non-transgenic.

This invention can also be applied to rapidly generate multiple chromosome substitution libraries from different backgrounds, and because of the omission of a transgenic step it becomes possible to avoid tedious transformation pipelines, identification of single transgenic events, characterisation of a transformant with sufficient knock-down of the target gene(s), and all other complications that come with transgenic approaches.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Construction of a Chromosome Substitution Library in Arabidopsis

Arabidopsis thaliana accessions Colombia (Col-0) and Landsberg erecta (Ler) were crossed to each other, and the resulting F1 hybrid population was used for the production of Doubled Haploid lines (DHs). This was achieved by pollinating the haploid inducer line described by Ravi & Chan (Nature 464 (2010), 615-619; US-2011/0083202; WO2011/044132) with pollen from Col×Ler F1 plants, and subsequently harvesting the progeny seeds, which were haploid, and genetically identical to the pollen grain from which they had been derived. DHs were subsequently obtained by spontaneous genome doubling in the haploid plants. A total of 101 DHs were obtained in this manner, and these plants were analysed with molecular markers homogenously covering all 5 chromosomes, to determine the origin of each chromosomal region that was covered by those markers. It was surprisingly found that only 23 of the DHs had recombination events in all 5 chromosomes, and that the other 78 DHs had at least one non-recombined chromosome. Such non-recombined chromosome was thus derived in its entirety from one of the parents of the starting hybrid (the Col×Ler F1), i.e. Col-0 or Ler.

Figure 1:
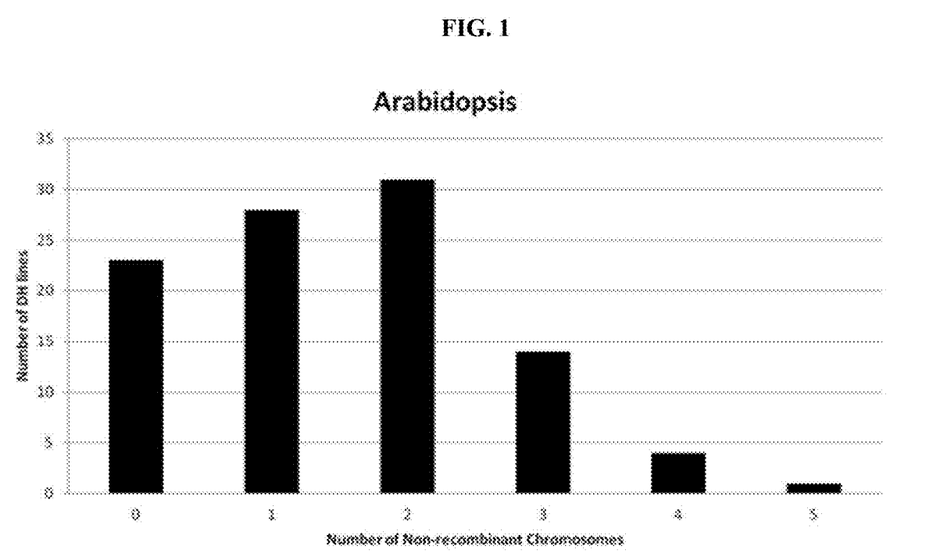
FIG. 1: An overview of the number of non-recombined parental chromosomes in a DH population of 101 lines, obtained from a Col-0×Ler hybrid by means of a haploid inducer system.

FIG. 1 illustrates the result of this analysis: 28 DHs had one non-recombined chromosome, 31 DHs had two non-recombined chromosomes, 14 DHs had three non-recombined chromosomes, 4 DHs had four non-recombined chromosomes, and one DH had five non-recombined chromosomes.

Figure 2:
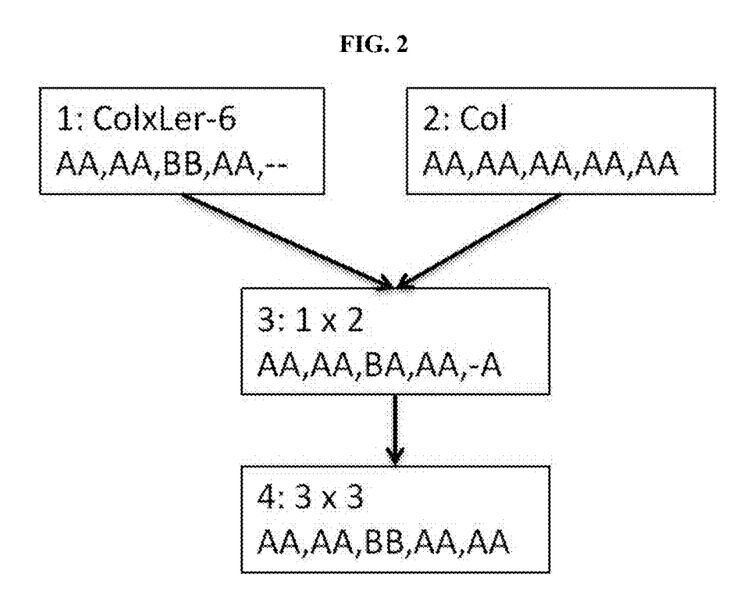
FIG. 2: An example of a crossing scheme for efficiently obtaining a specific chromosome substitution line for *Arabidopsis*, by applying the method of the present invention, as explained in Example 1. Each box represents a plant line where plant id, name and genotype is shown. When a plant is a product from a cross, the plant name is replaced by its parental names.

With these DHs it became possible to create specific chromosome substitution lines, comprising e.g. four Col-0 chromosomes and one Ler chromosome. One example of this approach is shown in FIG. 2. One of the lines (DH number 6 derived from the Col-0×Ler hybrid) was chosen for having four non-recombined parental chromosomes: chromosomes I, II and IV were entirely derived from the Col-0 accession (shown as "A" in FIG. 2), and chromosome III from the Ler accession (shown as "B" in FIG. 2), whereas chromosome V had undergone recombination and hence comprised fragments of both Col-0 and Ler (shown as "-" in FIG. 2). Due to the doubled haploid nature of the line, both copies of each of the chromosomes were identical to each other, as the plant was fully homozygous. This DH line was crossed to the original Col-0 accession (i.e. one of the parents of the starting hybrid), and the resulting F1 generation comprised plants that were fully homozygous for chromosomes I, II and IV (i.e. entirely derived from Col-0), and heterozygous for chromosome III (i.e. harbouring one intact copy of that chromosome from Col-0 and one intact copy of that chromosome from Ler). For chromosome V, the offspring of this cross comprised one intact copy of that chromosome from Col-0, and one recombined copy of that chromosome, comprising fragments of both Col-0 and Ler.

In the next step, this F1 was selfed, and among the resulting F2 progeny plants, a chromosome substitution line could be readily identified based on molecular marker profiles. This line comprised four non-recombined parental chromosomes from Col-0 (chromosomes I, II, IV and V), and one non-recombined parental chromosome from Ler. Other chromosome substitution lines could be made in a similar manner, by combining specific pairs of DHs with each other and/or with the parents of the starting hybrid, such that ultimately a complete chromosome substitution library comprising 32 distinct lines can be obtained.

Starting from the original accessions (Col-0 and Ler), the creation of this chromosome substitution line had thus merely taken, in total, three crosses and one DH step, in this example. The exact duration of this procedure thus depends largely on the generation time of the plant species (the time needed to complete the life cycle, from seed to seed) and on the availability of a fast and efficient DH protocol.

Table 1 shows the DH population size that is required to identify (with 95% certainty) one DH lines with 0, 1, 2, 3, 4 or 5 non-recombined parental chromosomes, for a plant species with 5 chromosomes, such as *Arabidopsis*, under the assumption that 50% of the chromatids is recombined (i.e. that on average one cross-over event occurs per chromosome pair i.e. one crossover in the tetravalent stage in profase I of the first meiotic division between the non-sister chromatids. From this table it follows that the chance of identifying a DH line with 2 or 3 non-recombined parental chromosomes is much higher than the chance of identifying a DH line with none or 5 non-recombined parental chromosomes. To identify one DH line with 5 non-recombined chromosomes a population of about 95 DHs would be required. In our experiment, one DH line with 5 non-recombined chromosomes could be identified, with a population size of 101 plants. This is entirely consistent with the estimated 50% cross-over frequency.

TABLE 1

| Total # chromosomes | # non-recombined chromosomes | Probability assuming 50% non-recombined chromatids | # DHs needed to get 1 with 95% certainty |
|---|---|---|---|
| 5 Chromosomes | 0 | 0.03125 | 95 |
|  | 1 | 0.15625 | 18 |
|  | 2 | 0.3125 | 8 |
|  | 3 | 0.3125 | 8 |
|  | 4 | 0.15625 | 18 |
|  | 5 | 0.03125 | 95 |

Example 2

Construction of a Chromosome Substitution Library in Cucumber

Ovules of an elite hybrid of cucumber (*Cucumis sativus*) were used as the starting material for the production of Doubled Haploid (DH) lines. The hybrid had been produced by crossing two inbred cucumber lines, which were fully homozygous. DH production was essentially performed using the gynogenesis protocol described in European patent no. EP-0 374 755, and a total of 301 individual DH lines were obtained in this experiment. The parental lines of the starting hybrid were also available, and based on the full-genome sequence of both parental lines a large number of polymorphisms was identified between the two parental genomes. For molecular analysis of the DH lines a total of 108 polymorphisms were selected, and KASP assays were developed for them (chromosome I, II, III, IV, V, VI and VII were genotyped using 14, 18, 14, 10, 23, 16 and 13 marker assays, respectively). The cucumber genome has a haploid chromosome number of 7.

Subsequently the 301 DH lines were genotyped using the above-mentioned molecular markers, and this analysis revealed the presence and absence of recombination events in each of their 7 chromosomes. Surprisingly, a considerable number of DH lines possessed multiple non-recombined chromosomes. In three DH lines all 7 chromosomes had remained non-recombined:

ATB 101 had inherited 3 intact, non-recombinant chromosomes from the father line of the starting hybrid (chromosomes I, II and VII) and 4 intact, non-recombined chromosomes from the mother line of the starting hybrid (chromosomes III, IV, V and VI);

AUW 055 had inherited 2 intact chromosomes from the father line of the starting hybrid (chromosomes I and III) and 5 intact chromosomes from the mother line of the starting hybrid (chromosomes II, IV, V, VI and VII);

AVZ 067 had inherited 4 intact chromosomes from the father line of the starting hybrid (chromosomes I, II, III and VI) and 3 intact chromosomes from the mother line of the starting hybrid (chromosomes IV, V and VII).

Figure 3:
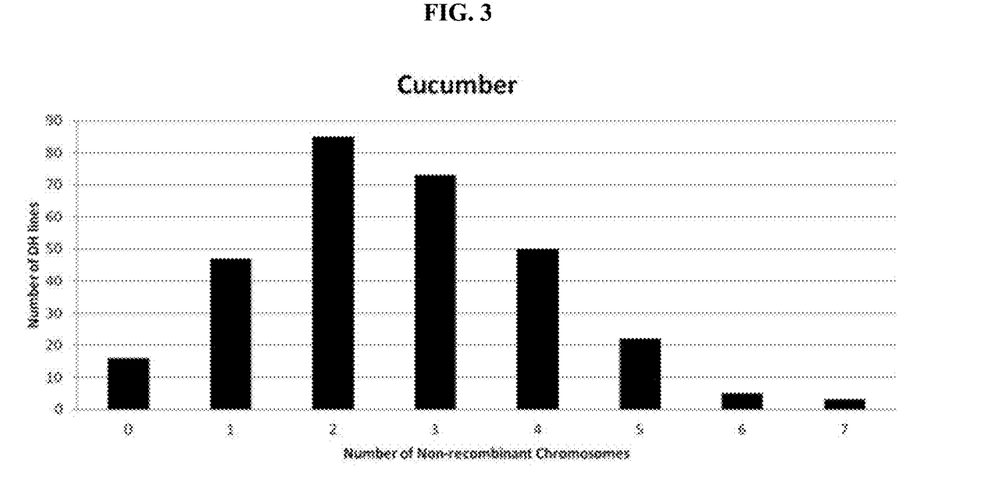
FIG. 3: An overview of the number of non-recombined parental chromosomes in a cucumber DH population of 301 lines, obtained from a cucumber hybrid by means of gynogenesis.

In five other DH lines one or more recombination event(s) was (were) detected in only one of the 7 chromosomes, while their other 6 chromosomes had remained non-recombined. Another 22 DH lines each had five non-recombined chromosomes and two recombined chromosomes. This observation revealed that meiotic recombination does not always occur, even when the recombination process is not interfered with, and that it is possible to identify spontaneous events in which a substantial number of the chromosomes (in some cases: all of them) have remained non-recombined. The entire dataset is shown in FIG. 3.

In the next step, specific DH lines were used for the efficient production of a complete chromosome substitution library for the starting hybrid. For species with 7 chromosomes such as cucumber, such a library consists of $2^7=128$ different DH lines, each of which comprises a different combination of the 7 chromosomes of the two parents of the starting hybrid. With the population of 301 DH lines as a starting point, a number of targeted crosses were carried out to maximise the efficiency of this approach. Below an example is given for one of the DH lines with 7 non-recombined chromosomes (AUW 055), but of course the strategy can be further optimised by also including the other two DH lines with 7 non-recombined chromosomes, and also the DH lines with less than 7 non-recombined chromosomes.

a) DH line AUW 055 was crossed to the mother line of the starting hybrid. In both crossing partners chromosomes II, IV, V, VI and VII were identical (derived from the mother of the starting hybrid), and the resulting F1 progeny of this cross was therefore homozygous for those 5 chromosomes, and heterozygous for chromosomes I and III (i.e. carrying a copy from the father of the starting hybrid and a copy from the mother of the starting hybrid). Self-pollination of an F1 progeny plant of this cross resulted in an F2 population in which chromosomes I and III were segregating, and among which the following four members of the chromosome substitution library could be identified, with "m" indicating chromosomes derived from the mother of the starting hybrid (maternal), and "p" indicating chromosomes derived from the father of the starting hybrid (paternal):

I(p)/II(m)/III(p)/IV(m)/V(m)/VI(m)/VII(m) (this line is identical to DH line AUW 055)
I(m)/II(m)/III(p)/IV(m)/V(m)/VI(m)/VII(m)
I(p)/II(m)/III(m)/IV(m)/V(m)/VI(m)/VII(m)
I(m)/II(m)/III(m)/IV(m)/V(m)/VI(m)/VII(m) (this line is identical to the mother line of the starting hybrid)

b) DH line AUW 055 was also crossed to the father line of the starting hybrid. In both crossing partners chromosomes I and III were identical (derived from the father of the starting hybrid), and the resulting F1 progeny of this cross was therefore homozygous for those two chromosomes, and heterozygous for chromosomes II, IV, V, VI and VII (i.e. carrying a copy from the father of the starting hybrid and a copy from the mother of the starting hybrid). Self-pollination of an F1 progeny plant of this cross resulted in an F2 population in which chromosomes II, IV, V, VI and VII were segregating, and among which the following 32 members of the chromosome substitution library could be identified, with "m" indicating chromosomes derived entirely (intact) from the mother of the starting hybrid (maternal), and "p" indicating chromosomes derived entirely (intact) from the father of the starting hybrid (paternal):

I(p)/II(p)/III(p)/IV(p)/V(p)/VI(p)/VII(p) (this line is identical to the father line of the starting hybrid)
I(p)/II(p)/III(p)/IV(p)/V(p)/VI(p)/VII(m)
I(p)/II(p)/III(p)/IV(p)/V(p)/VI(m)/VII(p)
I(p)/II(p)/III(p)/IV(p)/V(p)/VI(m)/VII(m)
I(p)/II(p)/III(p)/IV(p)/V(m)/VI(p)/VII(p)
I(p)/II(p)/III(p)/IV(p)/V(m)/VI(p)/VII(m)
I(p)/II(p)/III(p)/IV(p)/V(m)/VI(m)/VII(p)
I(p)/II(p)/III(p)/IV(p)/V(m)/VI(m)/VII(m)
I(p)/II(p)/III(p)/IV(m)/V(p)/VI(p)/VII(p)
I(p)/II(p)/III(p)/IV(m)/V(p)/VI(p)/VII(m)
I(p)/II(p)/III(p)/IV(m)/V(p)/VI(m)/VII(p)
I(p)/II(p)/III(p)/IV(m)/V(p)/VI(m)/VII(m)
I(p)/II(p)/III(p)/IV(m)/V(m)/VI(p)/VII(p)
I(p)/II(p)/III(p)/IV(m)/V(m)/VI(p)/VII(m) (this line is identical to DH line AVZ 067)
I(p)/II(p)/III(p)/IV(m)/V(m)/VI(m)/VII(p)
I(p)/II(p)/III(p)/IV(m)/V(m)/VI(m)/VII(m)
I(p)/II(m)/III(p)/IV(p)/V(p)/VI(p)/VII(p)
I(p)/II(m)/III(p)/IV(p)/V(p)/VI(p)/VII(m)
I(p)/II(m)/III(p)/IV(p)/V(p)/VI(m)/VII(p)
I(p)/II(m)/III(p)/IV(p)/V(p)/VI(m)/VII(m)
I(p)/II(m)/III(p)/IV(p)/V(m)/VI(p)/VII(p)
I(p)/II(m)/III(p)/IV(p)/V(m)/VI(p)/VII(m)
I(p)/II(m)/III(p)/IV(p)/V(m)/VI(m)/VII(p)
I(p)/II(m)/III(p)/IV(p)/V(m)/VI(m)/VII(m)
I(p)/II(m)/III(p)/IV(m)/V(p)/VI(p)/VII(p)
I(p)/II(m)/III(p)/IV(m)/V(p)/VI(p)/VII(m)
I(p)/II(m)/III(p)/IV(m)/V(p)/VI(m)/VII(p)
I(p)/II(m)/III(p)/IV(m)/V(p)/VI(m)/VII(m)
I(p)/II(m)/III(p)/IV(m)/V(m)/VI(p)/VII(p)
I(p)/II(m)/III(p)/IV(m)/V(m)/VI(p)/VII(m)
I(p)/II(m)/III(p)/IV(m)/V(m)/VI(m)/VII(p)
I(p)/II(m)/III(p)/IV(m)/V(m)/VI(m)/VII(m) (this line is identical to DH line AUW 055)

c) The example of step b) required a fairly large population size to identify all mentioned chromosome substitution lines, because five chromosomes were segregating in the progeny of this cross. In an alternative approach, further combinatorial optimisation was done by crossing DH lines AUW 055 and AVZ 067 to each other, and their F1 progeny was selfed to create all combinations of substitution lines in chromosome II and VI, with the other five chromosomes being derived from the paternal line. In parallel, DH line AVZ 067 was also crossed to the father line of the starting hybrid, and the F1 progeny from this cross was also selfed. In the F2, all substitution lines in chromosomes IV, V and VII were obtained, with the other four chromosomes being derived from the paternal line. These two crosses thus enabled the identification of the same chromosome substitution lines as detailed in step b) of this example above, but with a smaller population size.

d) After steps a) and b) or c) had been carried out as described, a total of 36 different members of the chromosome substitution library had thus already been obtained (including the DH lines AUW055, ATB101 and AVZ067, and both parents of the starting hybrid). By crossing specific lines from this subpopulation of 36 lines, it became possible to obtain all remaining members of the library, by efficient combination of the available parental lines, DHs and chromosome substitution lines. In this manner a complete chromosome substitution library could be constructed for the starting hybrid cucumber plant, consisting of 128 different lines.

Figure 4:
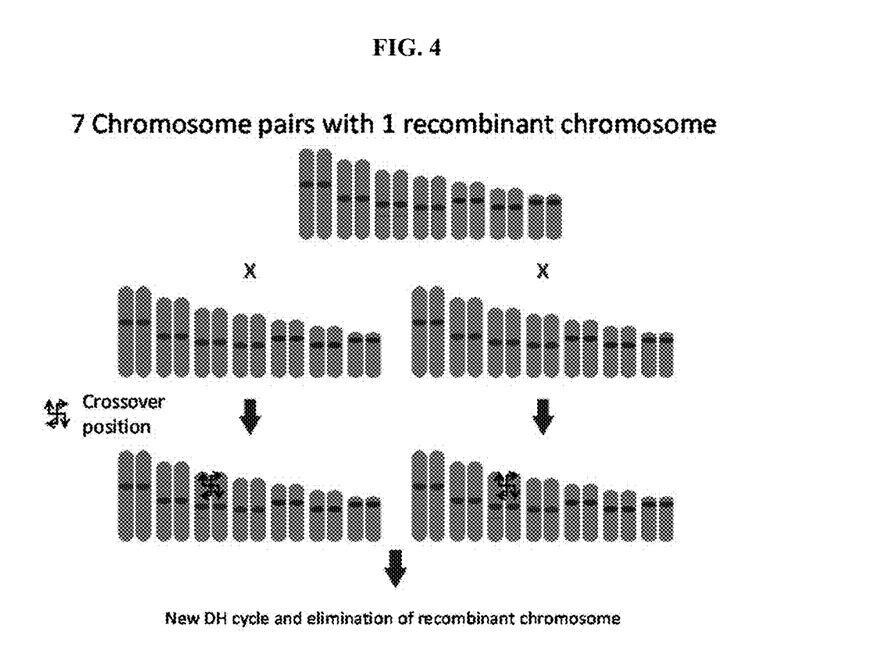
FIG. 4: An example of the use of a line with one recombinant chromosome and six non-recombinant chromosomes (for a species with a genome consisting of 7 chromosome pairs) in the method of the present invention. Said line is combined with the two original parental lines of the starting hybrid, and in subsequent cycles of DH production the recombinant chromosome can be eliminated.

In FIG. 4 the use of a line with one recombinant chromosome and six non-recombinant chromosomes (for a species with a genome consisting of 7 chromosome pairs) in the method of the present invention is shown schematically. Said line is combined with the two original parental lines of the starting hybrid, and in subsequent cycles of DH production the recombinant chromosome can be eliminated.

Figure 5A:
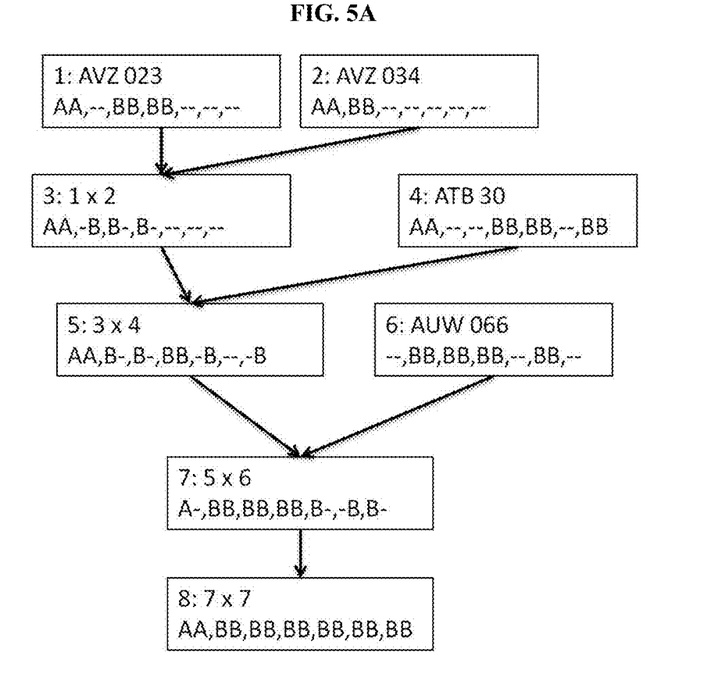
FIG. 5A: An example of a crossing scheme for obtaining a specific chromosome substitution line (shown in FIG. 5B) without using parents of the starting hybrid, in cucumber. Each box represents a plant line where plant id, name and genotype is shown. When a plant is a product from a cross, the plant name is replaced by its parental names.
Figure 5B:
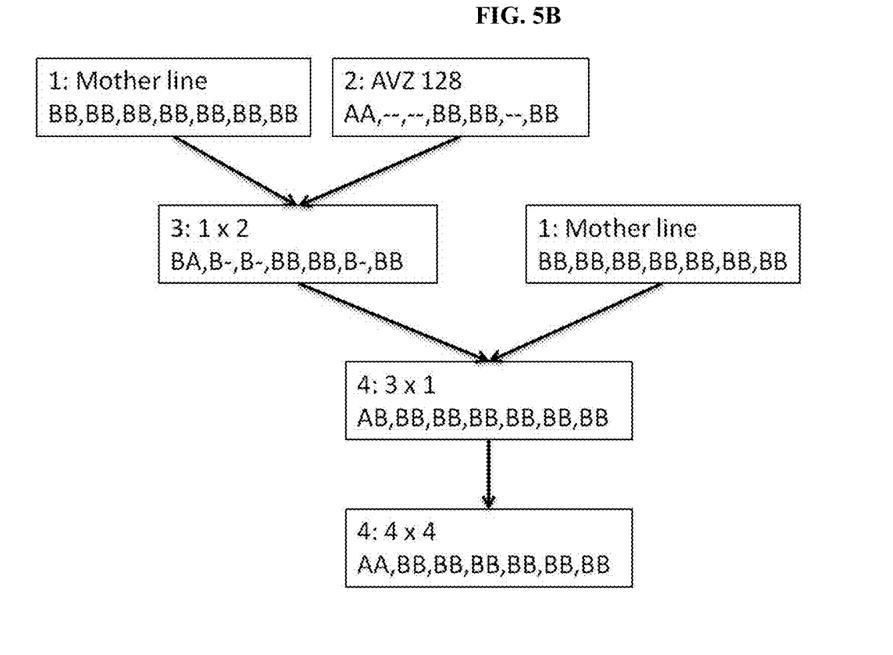
FIG. 5B: An example of applying the method of the present invention. An example crossing scheme for efficiently obtaining a specific chromosome substitution line by using parents of the starting hybrid in cucumber. Each box represents a plant line where plant id, name and genotype is shown. When a plant is a product from a cross, the plant name is replaced by its parental names.

If the parental lines of the starting hybrid are not available, it is still possible to create chromosome substitution lines and libraries, although the entire procedure may then take a few additional generations as compared to the above example. This is illustrated in FIGS. 5A and 5B. FIG. 5A illustrates that, starting from the 301 cucumber DH lines obtained in this experiment, it would take at least 4 generations to create a chromosome substitution line having one intact, non-recombined chromosome I from the mother line of the starting hybrid and 6 intact, non-recombined chromosomes (II, III, IV, V, VI and VII) from the father line of the starting hybrid. Exactly the same chromosome substitution line can be created within 3 generations, by identifying optimal DH lines and by using those along with the father line of the starting hybrid (as shown in FIG. 5B).

Table 2 illustrates that one would expect to identify at least one DH line with 7 non-recombined chromosomes among a population of about 382 DH lines, with an average cross-over frequency of 50%. In the actual example described here for cucumber no less than three such lines could be identified, in a population of 301 plants. This may indicate that 50% was not an accurate estimate for the actual recombination rate in this experiment, and that the actual recombination rate in this experiment was lower than 50%.

TABLE 2

| Total # chromosomes | # non-recombined chromosomes | Probability assuming 50% non-recombined chromatids | # DHs needed to get 1 with 95% certainty |
|---|---|---|---|
| 7 chromosomes | 0 | 0.0078125 | 382 |
| | 1 | 0.0546875 | 54 |
| | 2 | 0.1640625 | 17 |
| | 3 | 0.2734375 | 10 |
| | 4 | 0.2734375 | 10 |
| | 5 | 0.1640625 | 17 |
| | 6 | 0.0546875 | 54 |
| | 7 | 0.0078125 | 382 |

Depending on the probability to inherit a chromosome without recombination, this will result in a specific fraction of offspring with (in case of cucumber) 7, 6, 5, 4, 3, 2, 1, or 0 non-recombined chromosomes. The probability of each fraction can be calculated as follows:

$$\frac{M!}{N!(N-M)!} \cdot P^M \cdot (1-P)^{(N-M)}$$

with N=total number of chromosomes, M the total number of non-recombinant chromosomes, and P the expected probability of inheritance of non-recombined chromosomes (here assuming that the probability is equal for all chromosomes). For cucumber (N=7), table 2 shows the expected fraction of plants with M non-recombined chromosomes for P=0.5.

To calculate the probability to obtain plants with a specific combination of non-recombinant chromosomes (e.g. the combination of 4 maternal and 3 paternal chromosomes in a total of 7 non-recombinant chromosomes), the following formula can be used:

$$\frac{X!}{M!(M-X)!}$$

with M the total number of non-recombined chromosomes (as in the formula above) and X the number of non-recombined chromosomes from one parent.

By adding a correction factor $2^M$, these formulae can be combined to calculate the expected fractions of specific non-recombined chromosome combinations $$\frac{X!}{2^M M!(M-X)!} \cdot \frac{M!}{N!(N-M)!} \cdot P^M \cdot (1-P)^{(N-M)}$$

These formulas assume that each chromosome has an equal probability to inherit without recombination. However, chromosomes might have non-equal probabilities to be inherited without recombination. In this case, the expected probability will be the result of a summation over all possible product combinations of non-recombined and recombined probabilities of inheritance. For example, for cucumber there are seven possible combinations of six non-recombinant and one recombinant chromosome, as follows (with 0 indicating the recombinant chromosome):

| 1 | 2 | 3 | 4 | 5 | 6 | 7 |
|---|---|---|---|---|---|---|
| 1 | 1 | 1 | 1 | 1 | 1 | 0 |
| 1 | 1 | 1 | 1 | 1 | 0 | 1 |
| 1 | 1 | 1 | 1 | 0 | 1 | 1 |
| 1 | 1 | 1 | 0 | 1 | 1 | 1 |
| 1 | 1 | 0 | 1 | 1 | 1 | 1 |
| 1 | 0 | 1 | 1 | 1 | 1 | 1 |
| 0 | 1 | 1 | 1 | 1 | 1 | 1 |

Filling in the chromosome-specific probability of inheritance of a non-recombined chromosome $P_i$ at each position where there is a 1 and $(1-P_1)$ where there is a 0 in formula 3, then multiplying the probabilities in all rows, and adding up the different products will give the overall probability to obtain a DH-plant with six non-recombined chromosomes.

Example 3

Construction of a Chromosome Substitution Library in Barley

Figure 6:
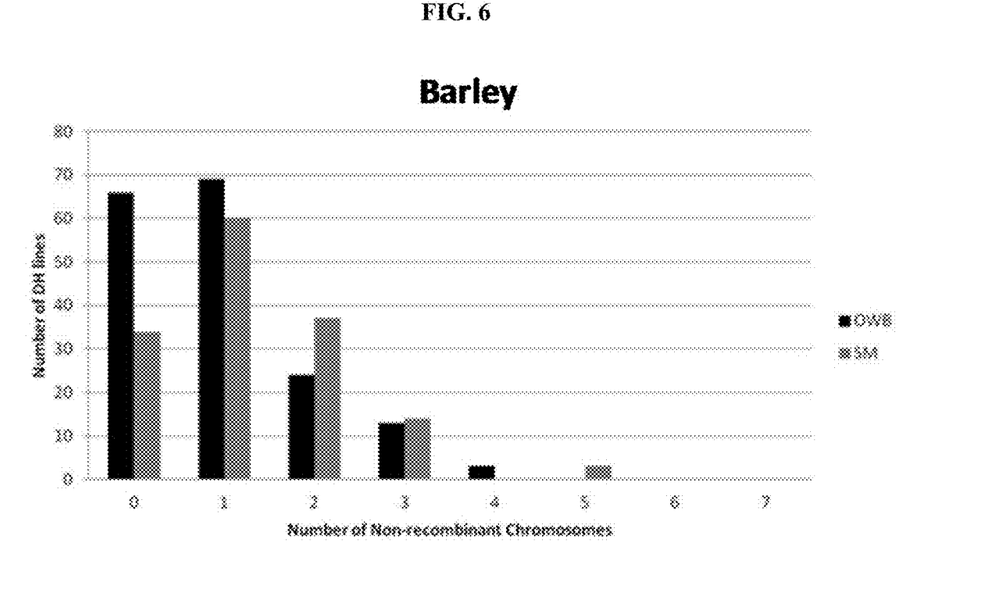
FIG. 6: An overview of the number of non-recombined parental chromosomes in barley DH populations OWB and SM, consisting of 175 and 148 lines, respectively.

Two barley DH populations—Oregon Wolfe Barley (OWB) and a DH population derived from a 'Steptoe'× 'Morex' cross (SM)—were analysed for the occurrence of non-recombined chromosomes in their genome. The OWB population consisted of 175 DH lines, which had been genotyped with a total of 444 molecular markers, and the SM population consisted of 148 DH lines, which had been genotyped with a total of 798 molecular markers (Cistué et al. 2011, Theor. Appl. Genet. 122: 1399-1410; Kleinhofs et al. 1993, Theor. Appl. Genet. 86:705-712). In both populations, the inventors of the present invention could identify individual DH lines with non-recombined chromosomes, and the result of this analysis is shown in FIG. 6. The OWB population comprised a total of 175 DHs, of which 66 lines did not have any non-recombined chromosomes, 69 lines had one non-recombined chromosome, 24 lines had two non-recombined chromosomes, 13 lines had three non-recombined chromosomes, and 3 lines had four non-recombined chromosomes.

The SM population comprised a total of 148 DHs, and here 34 of the DH lines did not have any non-recombined chromosomes, 60 lines had one non-recombined chromosome, 37 lines had two non-recombined chromosomes, 14 lines had three non-recombined chromosomes, none of the lines had four non-recombined chromosomes, and 3 lines had five non-recombined chromosomes.

The barley genome has a haploid chromosome number of 7, and the fact that no lines were found with 6 or 7 non-recombined chromosomes in either of these two populations is presumably due to the small size of the DH population. Theoretically, one would expect that at least one line with 7 non-recombined chromosomes would be found among a population of about 382 DH lines, as is illustrated in Table 2 for an average cross-over frequency of 50%.

Figure 7:
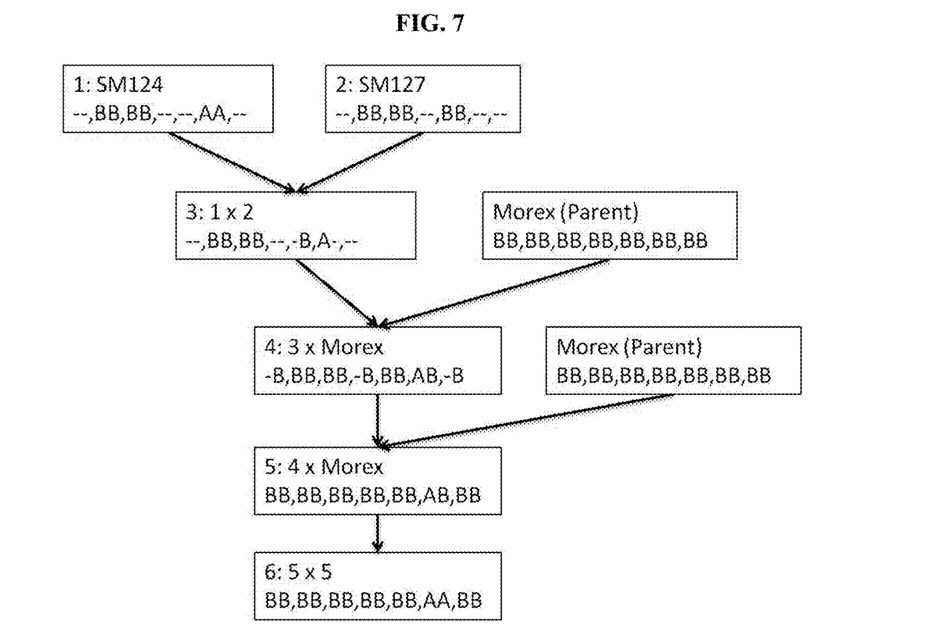
FIG. 7: An example of a crossing scheme for efficiently obtaining a specific chromosome substitution line for barley, by applying the method of the present invention, as explained in Example 3. Each box represents a plant line where plant id, name and genotype is shown. When a plant is a product from a cross, the plant name is replaced by its parental names.

As in the previous examples, it is possible to use these limited DH populations as a starting point for the creation of chromosome substitution lines. This is illustrated in FIG. 7. From the SM population (with as starting hybrid the F1 from a cross between the Steptoe and Morex accessions) two specific DHs are selected, which each have 3 non-recombined chromosomes in their genome: DH line SM124 has inherited intact chromosomes II and III from Morex ("B" in FIG. 7) and chromosome VI from Steptoe ("A" in FIG. 7), whereas DH line SM127 has inherited intact chromosomes II, III and V from Morex. The other chromosomes had undergone recombination, and thus comprise genomic fragments from both parents, Morex and Steptoe ("-" in FIG. 7). Crossing DH lines SM124 and SM127 results in F1 offspring with two intact non-recombined copies of chromosomes II and III from Morex, one intact non-recombined copy of chromosome V from Morex and one intact non-recombined copy of chromosome VI from Steptoe. An F1 individual is subsequently crossed to the original Morex accession (one of the two parents of the starting hybrid), and among the resulting progeny it is readily possible to identify (based on molecular marker profiles) individuals that are homozygous for the intact non-recombined chromosomes II, III, IV and V, heterozygous for the intact non-recombined chromosome VI (i.e. harbouring one parental copy of this chromosome from both Morex and Steptoe), and heterozygous for chromosomes I and VII (for each of which there is one recombined copy comprising genomic fragments from both parents, and one non-recombined copy of the parental chromosome from Morex).

This line is then again crossed to the original Morex accession, which results in the further fixation of chromosomes I and VII in some of the progeny plants, which are hence identical to Morex in all chromosomes but number VI, for which they are still heterozygous (i.e. carrying a copy of this chromosome from either parent of the starting hybrid, namely Morex and Steptoe). Selfing of such a specific individual results in a population that only segregates for chromosome VI, and among this population it is readily possible to identify (on the basis of molecular marker profiles) a chromosome substitution line in which chromosome VI has been derived from Steptoe (non-recombined and intact), and in which all other chromosomes have been derived from Morex (non-recombined and intact). Other chromosome substitution lines (and ultimately the entire chromosome substitution library consisting of 128 distinct individuals) can be created in a similar manner as described in this example.

Example 4

Construction of a Chromosome Substitution Library in Maize

Figure 8:
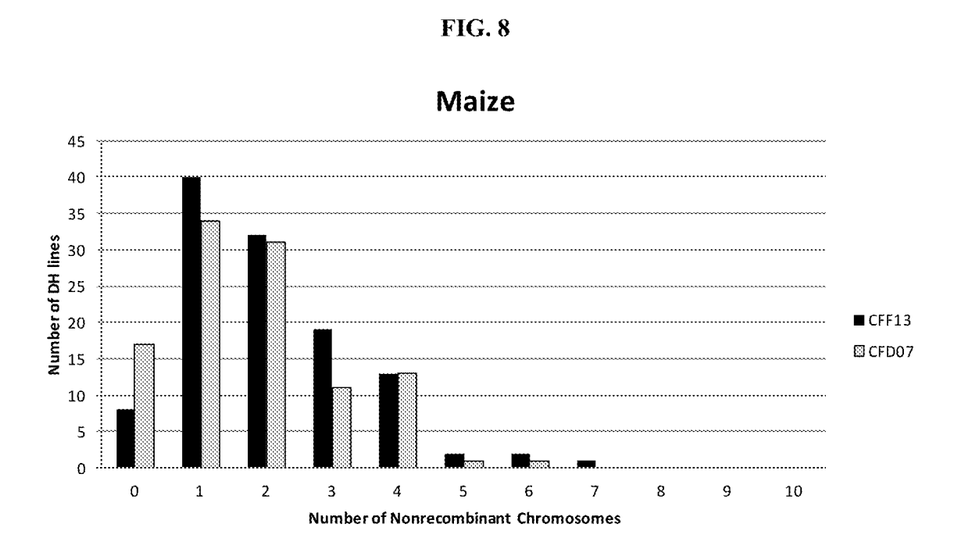
FIG. 8: An overview of the number of non-recombined parental chromosomes in maize DH populations CFF13 and CFD07, consisting of 117 and 108 lines, respectively.

From the study of Bauer et al. (Genome Biol. 14 (2013): R103), two maize DH populations were studied. These DH populations—CFF13 (a cross between two Flint gene pool parents) and CFD07 (a cross between two Dent gene pool parents)—had each been derived from hybrids between inbred lines. CFF13 consisted of 117 DH lines, genotyped using 6,379 polymorphic molecular markers, and CFD07 consisted of 108 lines, genotyped using 13,466 polymorphic molecular markers. As shown in FIG. 8, both populations comprised quite a few lines with at least one non-recombined parental chromosome. The highest number of non-recombined chromosomes encountered among these populations was six (in one line of the CFD07 population) and seven (in one line of the CFF13 population). If the DH populations would have been bigger, the chance of encountering lines with more non-recombined chromosomes would have been higher.

The obtained DHs with non-recombined parental chromosomes can again be crossed to each other and/or to the parents of the starting hybrids, to obtain specific chromosome substitution lines and ultimately the entire chromosome substitution library, comprising 1024 distinct lines.

Table 3 illustrates that for a plant species with 10 chromosomes (such as maize) and an average cross-over frequency of 50%, one would require a population of about 3,067 DH lines to identify one DH line with 10 non-recombined chromosomes, with a 95% certainty. The table also clearly shows that the chance of identifying a maize DH line with 2, 3, 4, 5, 6, 7 or 8 non-recombined chromosomes is much higher, and that only a very small DH population is required to have a very good chance at identifying at least one such DH line, using the method of the present invention.

As explained above, the availability of DH lines in which a subset of the chromosomes is already non-recombined allows for a better starting position in a second round of the method of the invention. For example, a DH line with 7 non-recombined chromosomes can be crossed with another DH line with 5 non-recombined chromosomes, wherein several of the non-recombined chromosomes are the same in both cases. This leads to an F1 in which several of the non-recombined, parental chromosomes are present in a homozygous state, and thus to a genomic situation that has become much less complex. By producing DHs from this F1 and subsequently crossing some of those DHs to other strategically selected lines (other DHs, chromosome substitution lines or parental lines of the starting hybrid) it is feasible to create more chromosome substitution lines, and suitably a complete or incomplete chromosome substitution library.

TABLE 3

| Total # chromosomes | # non-recombined chromosomes | Probability assuming 50% non-recombined chromatids | # DHs needed to get 1 with 95% certainty |
| --- | --- | --- | --- |
| 10 chromosomes | 0 | 0.000976563 | 3067 |
| | 1 | 0.009765625 | 306 |
| | 2 | 0.043945313 | 67 |
| | 3 | 0.1171875 | 25 |
| | 4 | 0.205078125 | 14 |
| | 5 | 0.24609375 | 11 |
| | 6 | 0.205078125 | 14 |
| | 7 | 0.1171875 | 25 |
| | 8 | 0.043945313 | 67 |
| | 9 | 0.009765625 | 306 |
| | 10 | 0.000976563 | 3067 |

The invention is further described by the following numbered paragraphs:

1. Method for producing a chromosome substitution library, comprising:
   a) producing a population of DH lines from an at least partially heterozygous starting organism;
   b) identifying a first DH line in the population that has at least one non-recombined chromosome pair;
   c) identifying a matching second DH line in the population that has at least one non-recombined chromosome pair that is the same as the non-recombined chromosome pair of the first DH line, and at least one non-recombined chromosome pair that is different from the non-recombined chromosome pair of the first DH line;
   d) selecting the first DH line and the second DH line as a pair of parents, the progeny of which has at least three non-recombined chromosomes, at least two of which form a pair;
   e) repeating steps b), c) and d) one or more times on the DH population of the heterozygous starting organism, or repeating steps a)-d) on a DH population produced from a progeny plant of a pair of parents selected in step d), until preferably all chromosomes from the selected DH lines are non-recombined and preferably all possible combinations of the parental chromosomes are selected, to assemble a library of chromosome substitution lines.

2. Method of paragraph 1, wherein the starting organism is a plant.

3. Method of paragraph 1 or 2, wherein at least one of the DH lines selected in step d) is genetically identical to one of the two parents of the at least partially heterozygous starting organism or wherein instead of said DH line that is genetically identical to the parent the original parent is used as one member of the pair of parents in step d).

4. Method of paragraphs 1-3, wherein the at least partially heterozygous starting organism is a plant.

5. Library of substitution lines, obtainable by the method of any one of the paragraphs 1-4.

6. Library of paragraph 5, wherein in each of the substitution lines one chromosome pair is derived from the first parent of the heterozygous starting organism and the other chromosome pairs are derived from the second parent of the heterozygous starting organism.

Having thus described in detail preferred embodiments of the present invention, it is to be understood that the invention defined by the above paragraphs is not to be limited to particular details set forth in the above description as many apparent variations thereof are possible without departing from the spirit or scope of the present invention

What is claimed is:

1. A method for producing a chromosome substitution library, comprising:
   a) producing a population of DH lines from an at least partially heterozygous starting plant;
   b) identifying a first DH line in the population that has at least one non-recombined chromosome pair relative to the starting plant;
   c) identifying a matching second DH line in the population that has at least one non-recombined chromosome pair relative to the starting plant that is the same as the non-recombined chromosome pair of the first DH line, and at least one non-recombined chromosome pair that is different from the non-recombined chromosome pair of the first DH line;
   d) selecting the first DH line and the second DH line as a pair of parents, the progeny of which has at least three non-recombined chromosomes relative to the starting plant, at least two of which form a pair;
   e) repeating steps b), c) and d) one or more times on the DH population of the heterozygous starting plant;
   wherein the method does not comprise suppressing meiotic recombination.

2. A method for producing a chromosome substitution library, comprising:
   a) producing a population of DH lines from an at least partially heterozygous starting plant;
   b) identifying a first DH line in the population that has at least one non-recombined chromosome pair relative to the starting plant;
   c) identifying a matching second DH line in the population that has at least one non-recombined chromosome pair relative to the starting plant that is the same as the non-recombined chromosome pair of the first DH line, and at least one non-recombined chromosome pair that is different from the non-recombined chromosome pair of the first DH line;
   d) selecting the first DH line and the second DH line as a pair of parents, the progeny of which has at least three non-recombined chromosomes relative to the starting plant, at least two of which form a pair;
   e) repeating steps a)-d) on a DH population produced from a progeny plant of a pair of parents selected in step d);
   wherein the method does not comprise suppressing meiotic recombination.

3. The method of claim 1, wherein all chromosomes from the selected DH lines are non-recombined.

4. The method of claim 2, wherein all chromosomes from the selected DH lines are non-recombined.

5. The method of claim 1, wherein all possible combinations of the parental chromosomes are selected to assemble a library of chromosome substitution lines.

6. The method of claim 2, wherein all possible combinations of the parental chromosomes are selected to assemble a library of chromosome substitution lines.

7. The method as claimed in claim 1, wherein at least one of the DH lines selected in step d) is genetically identical to one of the two parents of the at least partially heterozygous starting plant.

8. The method as claimed in claim 2, wherein at least one of the DH lines selected in step d) is genetically identical to one of the two parents of the at least partially heterozygous starting plant or wherein instead of said DH line that is genetically identical to the parent the original parent is used as one member of the pair of parents in step d).

9. The method as claimed in claim 1, wherein instead of the DH line selected in step d) that is genetically identical to the parent the original parent is used as one member of the pair of parents in step d).

10. The method as claimed in claim 2, wherein instead of the DH line selected in step d) that is genetically identical to the parent the original parent is used as one member of the pair of parents in step d).

* * * * *

UNITED STATES PATENT AND TRADEMARK OFFICE
CERTIFICATE OF CORRECTION

| | | |
|---|---|---|
| PATENT NO. | : 11,001,839 B2 | Page 1 of 1 |
| APPLICATION NO. | : 15/373741 | |
| DATED | : May 11, 2021 | |
| INVENTOR(S) | : Robert Héléne Ghislain Dirks et al. | |

It is certified that error appears in the above-identified patent and that said Letters Patent is hereby corrected as shown below:

On the Title Page

The Assignee should be listed as shown below:
(73) Assignee: RIJK ZWAAN ZAADTEELT EN ZAADHANDEL B.V., De Lier (NL)

Signed and Sealed this
Tenth Day of August, 2021

Drew Hirshfeld
*Performing the Functions and Duties of the
Under Secretary of Commerce for Intellectual Property and
Director of the United States Patent and Trademark Office*